(12) United States Patent
Flohr et al.

(10) Patent No.: US 9,176,078 B2
(45) Date of Patent: Nov. 3, 2015

(54) X-RAY DETECTOR SYSTEM FOR A COMPUTED TOMOGRAPHY SCANNER AND COMPUTED TOMOGRAPHY DEVICE

(71) Applicant: SIEMENS AKTIENGESELLSCHAFT, Munich (DE)

(72) Inventors: Thomas Flohr, Uehlfeld (DE); Michael Grasruck, Nuremberg (DE); Karl Stierstorfer, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 54 days.

(21) Appl. No.: 14/031,117

(22) Filed: Sep. 19, 2013

(65) Prior Publication Data

US 2014/0126688 A1    May 8, 2014

(30) Foreign Application Priority Data

Sep. 28, 2012 (DE) .......................... 10 2012 217 759

(51) Int. Cl.
 *A61B 6/00* (2006.01)
 *G01N 23/04* (2006.01)
 *G01T 1/29* (2006.01)
(52) U.S. Cl.
 CPC .............. *G01N 23/046* (2013.01); *A61B 6/584* (2013.01); *G01T 1/2985* (2013.01); *G01N 2223/419* (2013.01); *G01N 2223/501* (2013.01)

(58) Field of Classification Search
 CPC .......... A61B 6/27; A61B 6/32; A61B 6/2985; A61B 6/4021; A61B 6/4488; A61B 6/5205; G01T 1/24; G01T 1/249; G01N 23/046
 USPC ....................................................... 378/4, 19
 See application file for complete search history.

(56) References Cited

U.S. PATENT DOCUMENTS

2006/0002508 A1    1/2006  Yahata
2006/0256922 A1*  11/2006  Imai et al. ..................... 378/116

FOREIGN PATENT DOCUMENTS

DE        102005031679 A1    2/2006

OTHER PUBLICATIONS

German Office Action Dated Aug. 8, 2013.

* cited by examiner

*Primary Examiner* — Courtney Thomas
(74) *Attorney, Agent, or Firm* — Harness, Dickey & Pierce, P.L.C.

(57) ABSTRACT

For improved sampling, an x-ray detector system for a computed tomography scanner is provided. In an embodiment, the x-ray detector system includes at least one detector row which includes a plurality of detector modules each having a plurality of detector elements. Along the at least one detector row, a first portion of the detector elements is arranged in a grid at a first grid spacing in relation to its respective neighboring detector elements, and a second portion of the detector elements is arranged in a grid at a second grid spacing in relation to its respective neighboring detector elements.

20 Claims, 3 Drawing Sheets

X-RAY DETECTOR SYSTEM FOR A COMPUTED TOMOGRAPHY SCANNER AND COMPUTED TOMOGRAPHY DEVICE

PRIORITY STATEMENT

The present application hereby claims priority under 35U.S.C. §119 to German patent application number DE 102012217759.0 filed Sep. 28, 2012, the entire contents of which are hereby incorporated herein by reference.

FIELD

The invention generally relates to an x-ray detector system for a computed tomography scanner and/or a computed tomography device.

BACKGROUND

In modern computed tomography imaging, in order to improve sampling in the image plane (in the β direction, where β is what is termed the fan angle, see e.g. FIG. 1; the fan angle denotes an angular distance of a detector element from a central ray 12; the central ray is the centermost x-ray of the beam, connecting a focal spot 10 of a utilized x-ray source to the center of a utilized x-ray detector 11), either a so-called quarter detector offset is set or a technique known as the flying focal spot technique is used for the x-ray source. In the case of the quarter detector offset, the x-ray detector and the focal spot of the x-ray source are adjusted relative to one another such that the central ray of the focal spot is not directed precisely into the center of the detector and precisely between two detector elements, but is incident offset relative thereto by a quarter of the grid spacing of the grid of the x-ray detector (=distance between the center points of neighboring detector elements). Accordingly, the central ray also does not run through the center of rotation of the computed tomography scanner, but is offset relative thereto by a quarter of a grid spacing a of the detector elements of the x-ray detector that is projected onto the center of rotation.

The reasoning behind the quarter offset is that direct measurement rays (fan angle β, projection angle α) and measurement rays complementary to the direct measurement rays, which complementary measurement rays were received after approximately one half-revolution of the image acquisition system (x-ray source and x-ray detector) and in which the x-ray detector and the x-ray source have swapped their position (fan angle β'=−β, projection angle α'=α+π+2β), are offset relative to one another by exactly half a grid spacing. As a result, during the reconstruction into a projection, direct and complementary measurement rays can be interleaved by means of an "effective" sampling grid a/2 and consequently realize an improvement in sampling. If no quarter offset is set, the positions of the complementary measurement rays coincide with and overlay the positions of the direct measurement rays, resulting in an effective sampling grid that is equal to the grid spacing of the x-ray detector and consequently achieving no improvement in the sampling.

Alternatively, a technique referred to as flying focal spot can also be employed for improving the sampling in the image plane. Through electromagnetic deflection of the focal spot in the x-ray source (x-ray tube assembly) the position of the focal spot on an anode plate is controlled so as to produce a displacement by half a grid spacing between successive projections.

A prerequisite for the use of flying focal spot technology is an x-ray tube assembly equipped with a corresponding electromagnetic deflection means, the deflection of the focal spot having to be precisely synchronized with the readout of the x-ray detector. Setting a quarter detector offset also requires the x-ray detector and the position of the focal spot in the x-ray tube assembly to be finely adjustable. Toward that end, it is either necessary for an electromagnetic focal spot deflection device which moves the focal spot to the desired position on the anode plate to be present in the x-ray tube assembly, or else for the x-ray tube assembly and the x-ray detector to be provided with precision adjustment mechanisms. These solutions are all more or less complicated, resource-intensive and expensive. In particular, a precondition for electromagnetic focal spot deflection (for the flying focal spot or even just for setting the position of the focal spot) is an x-ray tube assembly equipped with corresponding complex and costly deflection electronics.

SUMMARY

An embodiment of the present invention provides a possibility of achieving improved sampling in the image plane for a computed tomography scanner even without precision-mechanical adjustment of x-ray detector and focal spot or deflection device for offsetting the focal spot in the x-ray source. An x-ray detector system for a computed tomography scanner and a computed tomography device are disclosed. Advantageous embodiments of the invention are in each case the subject matter of the associated dependent claims.

An embodiment of the inventive x-ray detector system for a computed tomography scanner has at least one detector row comprising a plurality of detector modules, each of which has a plurality of detector elementswherein in the longitudinal direction of the detector row (i.e. in the direction of the fan angle β) a first portion of the detector elements is arranged in a grid having a first grid spacing relative to its respective neighboring detector elements and a second portion of the detector elements is arranged in a grid having a second grid spacing relative to its respective neighboring detector elements. If an embodiment of the inventive x-ray detector system is used in a computed tomography scanner, improved sampling can be achieved in a simple manner and even without adjustment or deflection of the focal spot.

Within the scope of an embodiment of the invention, a computed tomography device having an inventive x-ray detector system is provided, said device having a rotatable gantry, wherein the x-ray detector system is arranged in the gantry and an x-ray source is arranged opposite the x-ray detector system. By means of a computed tomography device of said kind it is possible to achieve improved sampling and hence improved image resolution in a simple manner without complicated adjustments.

BRIEF DESCRIPTION OF THE DRAWINGS

The invention and further advantageous embodiments according to features of the dependent claims are explained in more detail hereinbelow with reference to example embodiments schematically represented in the drawing, without the invention being thereby limited to the example embodiments. In the figures:

DETAILED DESCRIPTION OF THE EXAMPLE EMBODIMENTS

Figure 1:
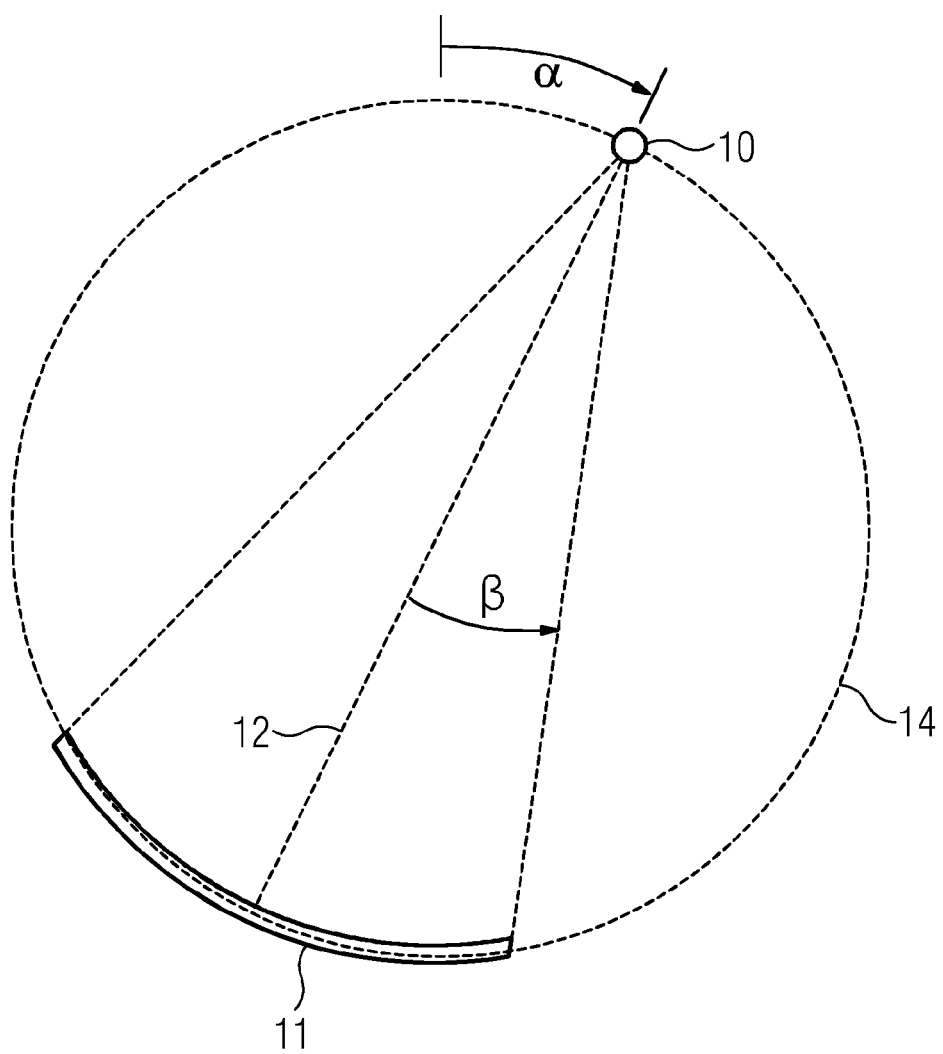
FIG. 1 shows a view of the geometry of a computed tomography scanner with x-ray source and x-ray detector.

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

An embodiment of the inventive x-ray detector system for a computed tomography scanner has at least one detector row comprising a plurality of detector modules, each of which has a plurality of detector elements, wherein in the longitudinal direction of the detector row (i.e. in the direction of the fan angle $\beta$) a first portion of the detector elements is arranged in a grid having a first grid spacing relative to its respective neighboring detector elements and a second portion of the detector elements is arranged in a grid having a second grid spacing relative to its respective neighboring detector elements. If an embodiment of the inventive x-ray detector system is used in a computed tomography scanner, improved sampling can be achieved in a simple manner and even without adjustment or deflection of the focal spot.

Regardless of the exact position of the focal spot of the x-ray source over the center of the x-ray detector (i.e. irrespective of the so-called "alignment" of the x-ray detector in detector channels), an improvement in sampling is achieved on average in all cases, whereby according to alignment the effective sampling grid is at maximum as large as the smallest grid spacing and in most cases (alignments) is even significantly smaller. This means that precision-mechanical adjustment devices can be dispensed with, and the x-ray source too requires no complex deflection mechanisms. This enables high-quality x-ray imaging to be realized while at the same time achieving a cost reduction, since simple x-ray sources "off the shelf" can be employed instead of specially developed x-ray sources, and permanently mounted x-ray detectors instead of detectors having precision adjustment mechanisms. Corresponding control and regulating mechanisms are likewise no longer necessary.

According to an embodiment of the invention, a group of at least two or more detector elements at the first grid spacing and a group of at least two or more detector elements at the second grid spacing are arranged alternately relative to their neighboring detector elements in continuous sequence in relation to the β direction. Thus, for example, a sequence of ten detector elements can in each case be provided at the first grid spacing and ten detector elements at the second grid spacing, etc. By means of a distribution of this kind the average effective sampling grid can be particularly easily and effectively reduced independently of the alignment.

According to another embodiment of the invention, the x-ray detector system comprises detector modules having exclusively detector elements at the same grid spacing in relation to their respective neighboring detector elements. This makes the production of the detector modules and consequently of the entire x-ray detector particularly economical in terms of resources.

Advantageously, the x-ray detector system comprises detector modules having detector elements at two different grid spacings. In this way a particularly simple installation of the x-ray detector can be carried out.

According to another embodiment of the invention, the x-ray detector system comprises detector elements at at least one further grid spacing that is different from the first and the second grid spacing in relation to their respective neighboring detector elements. By means of three or more different grid spacings it is possible to reduce the size of the average effective sampling grid further and therefore improve the sampling and imaging even further.

According to another embodiment of the invention, all detector elements at the first grid spacing are in each case arranged adjacent to one another and all detector elements at the second grid spacing are in each case arranged adjacent to one another. Thus, for example, all detector elements on one side of the detector row can be arranged at the first grid spacing and those on the other side can be arranged at the second grid spacing. A reduction in the effective sampling grid can be achieved by this means also.

The following advantageously applies to the two grid spacings: $0.5 \cdot a_1 \leq a_2 \leq 0.99 \cdot a_1$, in particular $a_2 = 0.9 \cdot a_1$. Other size ratios may also be present.

According to another embodiment of the invention, the detector elements along the at least one detector row have a different length (and hence in general also different sensor surface areas), in particular as a function of their respective grid spacing. Thus, for example, a detector element having a proportionally greater length will also be used at the larger grid spacing than at the smaller grid spacing. Two or more detector element lengths or sensor surface sizes can be used. If detector elements of the same length are used at the greater grid spacing, larger interspaces must be arranged between the detector elements.

When detector elements of different length are used, it is advantageous to embody sensor surfaces of the detector elements in such a way that the sensor surfaces' coverage of the surface area that is to be irradiated is substantially uniform. It is desirable in particular to achieve a coverage of at least 70%.

By coverage is understood the surface area of the sensor surfaces in relation to the entire surface area of the detector elements. This is significantly less than 100%, since it is also necessary to accommodate switching elements on the detector element in addition to the sensor surfaces.

Within the scope of an embodiment of the invention, a computed tomography device having an inventive x-ray detector system is provided, said device having a rotatable gantry, wherein the x-ray detector system is arranged in the gantry and an x-ray source is arranged opposite the x-ray detector system. By means of a computed tomography device of said kind it is possible to achieve improved sampling and hence improved image resolution in a simple manner without complicated adjustments.

FIG. 1 schematically shows the geometric arrangements in a known computed tomography device having a curved x-ray detector 11 with at least one detector row and having an x-ray source with a focal spot 10. The x-ray detector 11 and the x-ray source are arranged opposite one another in a gantry (not shown) of the computed tomography device and can be moved on a circular path 14 around an isocenter. The x-ray source emits x-ray radiation, the so-called central ray 12 being directed essentially onto the center of the x-ray detector. The so-called fan angle β denotes an angular distance of a detector element (pixel element) from the central ray 12. During the rotation of the gantry, a plurality of projection images are recorded at different projection angles α and subsequently reconstructed accordingly, e.g. into 3D volume images. The general acquisition and reconstruction of computed tomography images are well-known.

The known x-ray detector 11 has a uniform grid which determines the arrangement of the detector elements, i.e. the grid spacings of the detector elements (center of one detector element to the center of the nearest-neighbor detector element) are the same. What is to be understood by the grid of the x-ray detector in the present context is not a mechanical grid, but rather a type of the arrangement in grid form.

Figure 2:
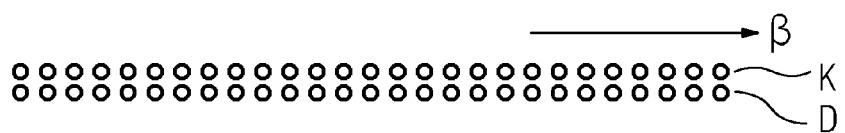
FIG. 2 shows a view of the offset between direct measurement rays and complementary measurement rays in known computed tomography scanners without offset or adjustment.

If the central ray of the x-ray source is aligned such that it impinges precisely on the center of the x-ray detector (i.e. is incident precisely between two detector elements), then the direct measurement rays and the so-called complementary measurement rays (measurement rays after approx. one half-revolution of the gantry, when x-ray detector and focal spot have swapped their positions) will be incident on the same positions and an effective sampling grid corresponding to the grid of the x-ray detector will be produced. FIG. 2 shows the positions of the direct measurement rays D and the complementary measurement rays K as a function of the fan angle β.

Figure 3:
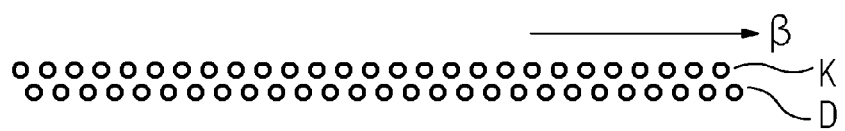
FIG. 3 shows a view of the offset between direct measurement rays and complementary measurement rays in known computed tomography scanners with quarter offset.

In such cases the so-called quarter detector offset is set in order to improve the sampling, which means that a precision-mechanical adjustment between x-ray detector and focal spot is performed so that the central ray deviates by a quarter of a (detector) grid from the center of the x-ray detector. Sampling is improved as a result of this adjustment, since the direct measurement rays D and the complementary measurement rays K, as shown in FIG. 3, are incident offset with respect to one another by a half grid spacing. The effective sampling grid of such an arrangement equals a/2, where a is the grid spacing. However, the device allowing such a fine adjustment is very complex and expensive.

An inventive x-ray detector system for computed tomography thus has at least two groups of detector elements which differ from one another in that they have different grid spacings in the direction of the fan angle β; the x-ray detector therefore has at least two different (detector) grids along its at least one detector row. A plurality of different embodiments may be present in order to implement the invention, e.g. in that the grids continuously alternate. Irrespective of an offset (such as the quarter offset) of the position of the focal spot of the x-ray source with respect to the center of the detector, sampling is improved on average in all cases as a result of the invention, the effective sampling grid during the sampling being at maximum as large as the smallest grid spacing. With certain alignments the effective sampling grid is even significantly smaller.

Figure 7:
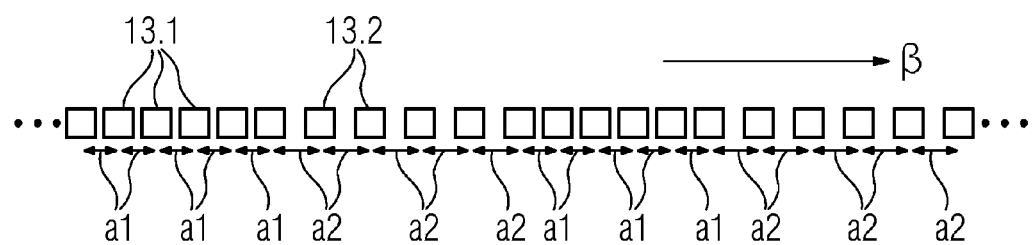
FIG. 7 shows an arrangement of detector elements of an x-ray detector system according to an embodiment of the invention.
Figure 8:
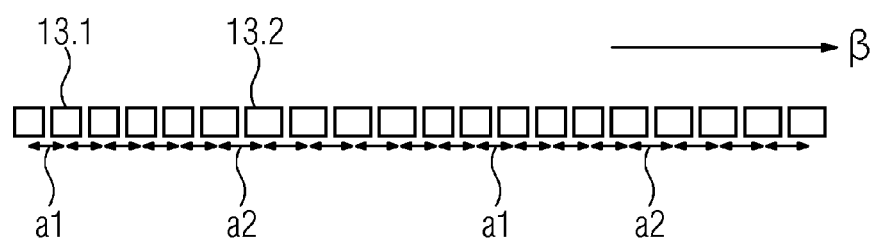
FIG. 8 shows a further arrangement of detector elements of an x-ray detector system according to an embodiment of the invention.

FIGS. 7 and 8 show details of detector rows of an inventive x-ray detector system which have first detector elements 13.1 at a first grid spacing $a_1$ and second detector elements 13.2 at a second grid spacing $a_2$ in the $\beta$ direction. In both cases a group of multiple first detector elements 13.1 at the first grid spacing $a_1$ alternates each time with a group of multiple second detector elements 13.2 at the second grid spacing $a_2$, etc. The groups each have at least two, e.g. five (as shown), ten or fifteen detector elements. In an x-ray detector system there is therefore present along the at least one detector row e.g. a sequence of ten first detector elements at a first grid spacing, followed by ten second detector elements at a second grid spacing, then again ten first detector elements, etc., in total from the beginning to the end of the detector row.

The different grid spacings can likewise be realized in different ways. In FIG. 7, the detector elements in the direction of the fan angle $\beta$ are equal in size, but are arranged at a greater interval from the neighboring detector element. In FIG. 8, the second detector elements 13.2 in the direction of the fan angle $\beta$ have a greater length than the first detector elements 13.1. The widths of all the detector elements (i.e. orthogonally to the longitudinal direction of the detector row) can be identical.

For example, the detector rows of an x-ray detector system are typically constructed in such a way that detector modules each having e.g. 16 or 20 detector elements are aligned sequentially in the $\beta$ direction. In order to implement the inventive x-ray detector, provision can be made to use detector modules having detector elements at two (or more) different grid spacings. Thus, for example, a detector module comprising twenty detector elements can have disposed on it an arrangement of ten first detector elements and ten second detector elements. The detector modules are concatenated in a suitable sequence such that e.g. a continuous sequence of in each case ten first and ten second detector elements is produced. A central ray aligned onto the center of the x-ray detector from the perspective of the focal spot impinges onto the detector row roughly in the center between two detector modules having different grid spacings. With an exact alignment (offset=0) and also with a less exact alignment, when e.g. the central ray is offset due to the mechanical retaining means by less than +/− five detector elements from the center of the detector row, with such an x-ray detector direct measurement rays onto first detector elements overlap with complementary measurement rays onto second detector elements (and vice versa). The positions of the complementary measurement rays therefore fall between the positions of the direct measurement rays.

In the case of the x-ray detector system according to the invention this results in a sampling grid which on average is as fine as or finer than the smaller of the grid spacings. Image quality is significantly improved as a result. What is involved here is not a fixed sampling grid as in the case of a conventional arrangement (e.g. a half grid spacing in the quarter offset), but a sampling grid that is different from measurement ray to measurement ray. The actual position of the focal spot over the x-ray detector can be determined once for a specific operating situation of the computed tomography device from a simple calibration measurement, e.g. by recording an image of a wire phantom. As a result the respective relative position of the grid spacings of the direct and complementary measurement rays is known and can be taken into account during the reconstruction.

Figure 4:
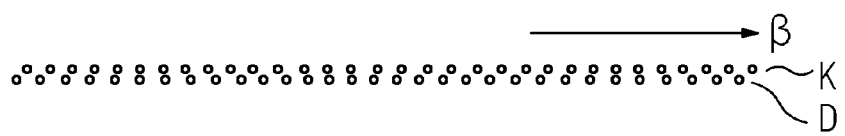
FIGS. 4 to 6 show a view of the offset between direct measurement rays and complementary measurement rays when an embodiment of the inventive x-ray detector system is used for different alignments.
Figure 5:
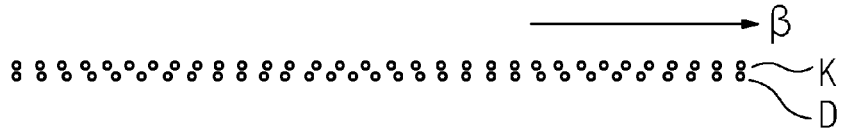
Figure 6:
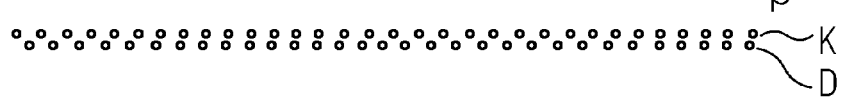

Three different sampling situations for different positions of the focal spot and hence of the central ray are shown in FIGS. 4 to 6, wherein in all cases an on average finer sampling and consequently better image representation is achieved than in the situation shown in FIG. 2 (same grid spacings without offset). The examples are shown for an overlaying of direct measurement rays D and complementary measurement rays K in the case of an x-ray detector which has ten first detector elements at first grid spacing $a_1$ and ten second detector elements at second grid spacing $a_2$ in the $\beta$ direction in each case, where $a_2=0.9\ a_1$. FIG. 4 shows an offset of 0.25 detector elements (quarter offset), in FIG. 5 there is no offset, and in FIG. 6 an offset of 2.75 detector elements is shown. Regardless of the offset (also called alignment) an on average improved sampling results in all cases with an effective sampling grid $a_{eff} \leq a_2$.

The smaller grid spacing can be e.g. between 0.5 and 0.99 times as large as the larger grid spacing. Other sizes are also possible.

In order to implement the x-ray detector according to the invention, provision can also be made to use detector modules which for each detector module type include only detector elements having equal grid spacings, although in that case the detector module types differ from one another in terms of the size of the grid spacings of their detector elements. The detector row of the x-ray detector is then populated with detector modules of different types. It can be provided in this case to realize an alternating arrangement of a detector module of a first type (e.g. having first detector elements at first grid spacings) and a detector module of a second type (e.g. having second detector elements at second grid spacings). It can e.g. also be provided to populate the detector row on one side with respect to its center (in the $\beta$ direction) with detector modules having first detector elements at first grid spacings and the other side of the detector row with detector modules having second detector elements at second grid spacings. Any desired arrangements are conceivable.

An x-ray detector can have one or more detector rows. In addition to the detector elements having first and second grid spacings, further detector elements having other grid spacings may also be present.

The invention can be briefly summarized as follows: For improved sampling, an x-ray detector system for a computed tomography scanner is provided, said x-ray detector system comprising at least one detector row having a plurality of detector modules each having a plurality of detector elements, wherein along the at least one detector row a first portion of the detector elements is arranged in a grid having a first grid spacing $a_1$ in relation to its respective neighboring detector elements and a second portion of the detector elements is arranged in a grid having a second grid spacing $a_2$ in relation to its respective neighboring detector elements.

What is claimed is:

1. An x-ray detector system for a computed tomography scanner, said x-ray detector system comprising:
   at least one detector row including a plurality of detector modules, each of the plurality of detector modules including a plurality of detector elements, wherein
      in the direction of a fan beam angle along the at least one detector row, a first portion of the detector elements is arranged in a grid having a first grid spacing in relation to respective neighboring detector elements and a second portion of the detector elements is arranged in a grid having a second grid spacing in relation to respective neighboring detector elements.

2. The x-ray detector system of claim 1, wherein a group of at least two first detector elements at the first grid spacing and a group of at least two second detector elements at the second grid spacing are arranged alternately along the at least one detector row in a continuous sequence in relation to respective neighboring detector elements.

3. The x-ray detector system of claim 1, wherein the plurality of detector modules include detector elements at the same grid spacing in relation to respective neighboring detector elements.

4. The x-ray detector system of claim 1, wherein the plurality of detector modules include detector elements at two different grid spacings in relation to respective neighboring detector elements.

5. The x-ray detector system of claim 1, further comprising:
   additional detector elements at at least one further grid spacing, the at least one further grid spacing being different from the first and the second grid spacing in relation to respective neighboring detector elements.

6. The x-ray detector system of claim 1, wherein
   all first detector elements having the first grid spacing are arranged adjacent to one another; and
   all second detector elements having the second grid spacing are arranged adjacent to one another.

7. The x-ray detector system of claim 1, wherein
   $a_1$ is the first grid spacing;
   $a_2$ is the second grid spacing; and
   $0.5 \cdot a_1 \leq a_2 \leq 0.99 \cdot a_1$ applies to the first and second grid spacings.

8. The x-ray detector system of claim 1, wherein the detector elements along the at least one detector row have at least two different lengths.

9. The x-ray detector system of claim 1, wherein sensor surfaces of the detector elements are embodied such that coverage by the sensor surfaces of the surface area that is to be irradiated is substantially uniform.

10. A computed tomography device comprising:
    the x-ray detector system of claim 1; and
    a rotatable gantry, wherein
      the x-ray detector system is arranged in the rotatable gantry, and
      an x-ray source is arranged opposite the x-ray detector system.

11. The x-ray detector system of claim 7, wherein $a_2 = 0.9 \cdot a_1$ applies to the first and second grid spacings.

12. The x-ray detector system of claim 8, wherein the detector elements along the at least one detector row have at least two different lengths as a function of respective grid spacing.

13. The computed tomography device of claim 10, wherein a group of at least two first detector elements at the first grid spacing and a group of at least two second detector elements at the second grid spacing are arranged alternately along the at least one detector row in a continuous sequence in relation to respective neighboring detector elements.

14. The computed tomography device of claim 10, wherein the plurality of detector modules include detector elements at the same grid spacing in relation to respective neighboring detector elements.

15. The computed tomography device of claim 10, wherein the plurality of detector modules include detector elements at two different grid spacings in relation to respective neighboring detector elements.

16. The computed tomography device of claim 10, wherein the x-ray detector system further comprises:
    additional detector elements at at least one further grid spacing, the at least one further grid spacing being different from the first and the second grid spacing in relation to respective neighboring detector elements.

17. The computed tomography device of claim 10, wherein
    all first detector elements having the first grid spacing are arranged adjacent to one another; and
    all second detector elements having the second grid spacing are arranged adjacent to one another.

18. The computed tomography device of claim 10, wherein
    $a_1$ is the first grid spacing;
    $a_2$ is the second grid spacing; and
    $0.5 \cdot a_1 \leq a_2 \leq 0.99 \cdot a_1$ applies to the first and second grid spacings.

19. The computed tomography device of claim 10, wherein the detector elements along the at least one detector row have at least two different lengths.

20. The computed tomography device of claim 19, wherein the detector elements along the at least one detector row have at least two different lengths as a function of respective grid spacing.

* * * * *